(12) United States Patent
Sato et al.

(10) Patent No.: US 10,537,230 B2
(45) Date of Patent: Jan. 21, 2020

(54) ENDOSCOPE INCLUDING BENDING OPERATION MECHANISM

(71) Applicant: OLYMPUS CORPORATION, Tokyo (JP)

(72) Inventors: Yuta Sato, Hachioji (JP); Toshihiro Matsui, Fussa (JP); Takashi Matsunaga, Hachioji (JP); Yuta Sekiguchi, Hachioji (JP); Koji Yasunaga, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 114 days.

(21) Appl. No.: 15/471,126

(22) Filed: Mar. 28, 2017

(65) Prior Publication Data

US 2017/0196435 A1  Jul. 13, 2017

Related U.S. Application Data

(63) Continuation of application No. PCT/JP2015/075897, filed on Sep. 11, 2015.

(30) Foreign Application Priority Data

Oct. 3, 2014  (JP) ................. 2014-204884

(51) Int. Cl.
*A61B 1/005* (2006.01)
*A61B 1/00* (2006.01)
(Continued)

(52) U.S. Cl.
CPC ........ *A61B 1/0052* (2013.01); *A61B 1/00039* (2013.01); *A61B 1/0057* (2013.01);
(Continued)

(58) Field of Classification Search
CPC ..... A61B 1/005; A61B 1/0051; A61B 1/0052; A61B 1/0053; A61B 1/0055;
(Continued)

(56) References Cited

U.S. PATENT DOCUMENTS

2004/0267093 A1  12/2004  Miyagi et al.
2008/0275303 A1  11/2008  Koitabashi

FOREIGN PATENT DOCUMENTS

EP    1 946 694 A1    7/2008
JP    6-277176        10/1994
(Continued)

OTHER PUBLICATIONS

English translation of International Preliminary Report on Patentability dated Apr. 13, 2017 together with the Written Opinion received in related International Application No. PCT/JP2015/075897.

(Continued)

*Primary Examiner* — Ryan N Henderson
(74) *Attorney, Agent, or Firm* — Scully, Scott, Murphy & Presser, P.C.

(57) ABSTRACT

A bending operation mechanism of the endoscope is an operating section to operate a bending section, and a boot section to cover the main body of the operating section in a watertight manner by causing a tiltable operating lever provided at the frame section to pass through the boot section, includes a watertight fixing portion on its periphery. The endoscope includes a first fixing member engaged with the locking section of the frame section and locked unrotatably in the watertight fixing portion of the boot section to press the watertight fixing portion from an outer periphery side such that the watertight fixing portion is made watertight, and a second fixing member screwed with the frame section to fix the first fixing member on the frame section.

3 Claims, 8 Drawing Sheets

(51) Int. Cl.
*A61B 34/00* (2016.01)
*G02B 23/24* (2006.01)
(52) U.S. Cl.
CPC .......... *A61B 1/00066* (2013.01); *A61B 34/74* (2016.02); *G02B 23/2476* (2013.01); *A61B 2034/742* (2016.02)
(58) Field of Classification Search
CPC ... A61B 1/0056; A61B 1/0057; A61B 1/0058; A61B 1/008; A61B 1/01; A61B 2034/742
See application file for complete search history.

(56) References Cited

FOREIGN PATENT DOCUMENTS

| | | |
|---|---|---|
| JP | 2004-321612 | 11/2004 |
| JP | 2006-192201 | 7/2006 |
| JP | 2007-130309 A | 5/2007 |
| JP | 2009-89955 A | 4/2009 |
| JP | 2011-50643 A | 3/2011 |
| JP | 2013-39188 A | 2/2013 |
| WO | 2013/114913 A1 | 8/2013 |

OTHER PUBLICATIONS

International Search Report dated Dec. 15, 2015 received in PCT/JP2015/075897.
Japanese Office Action dated Jul. 19, 2016 received in JP 2016-529480.
Extended Supplementary European Search Report dated Jun. 8, 2018 in European Patent Application No. 15 84 7560.8.

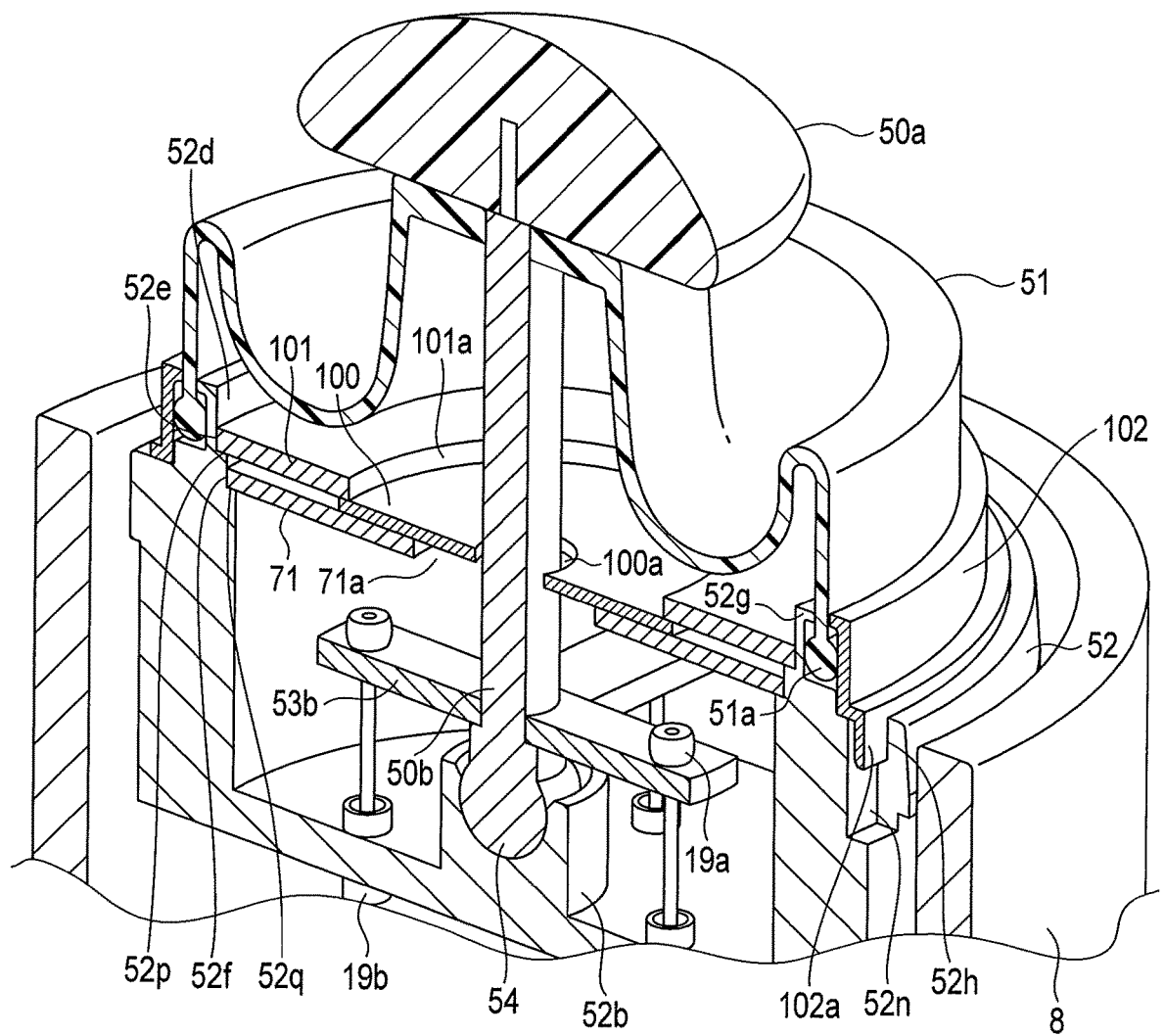
F I G. 8

ENDOSCOPE INCLUDING BENDING OPERATION MECHANISM

CROSS-REFERENCE TO RELATED APPLICATIONS

This is a Continuation application of PCT Application No. PCT/JP2015/75897, filed Sep. 11, 2015, which was published under PCT Article 21(2) in Japanese.

This application is based upon and claims the benefit of priority from prior Japanese Patent Application No. 2014-204884, filed Oct. 3, 2014 the entire contents of which are incorporated herein by references.

BACKGROUND OF THE INVENTION

1. Field of the Invention

The present invention relates to a bending operation mechanism having a watertight structure and an endoscope including the bending operation mechanism.

2. Description of the Related Art

Recently, endoscopes have widely been used in the medical field and the industrial field to examine and treat a cavity and a hollow organ of the body. These endoscopes include a thin elongated insertion section to be inserted into the cavity and hollow organ of the body. As the insertion section, a flexible scope bent in accordance with the bending state of an insertion path and a rigid scope used chiefly for operations and the like are known. The flexible scope includes a bending section at its distal end, and the bending section can freely be bent in a desired direction in accordance with a user's hand operation.

As disclosed in, for example, Patent Literature 1: Jpn. Pat. Appln. KOKAI Publication No. 2009-89955, as a conventional endoscope, an endoscope is known in which a user tilts a joystick-type operating lever provided on an operating section toward an arbitrary direction to pull an operating wire and render a bending section in a desired bending state.

In medical endoscopes, an insertion section used in a body cavity has a watertight structure to prevent water drops and blood from entering the body cavity, and an operating section, which is formed integrally with the insertion section as one unit, needs a reasonable watertight structure to irrigate and sterilize the operating section after it is used.

The conventional endoscope including a joystick lever type operating section is so configured that even though a joystick lever is tilted to any position within a movable range of the joystick lever, the water-tightness between the joystick lever and the exterior member is always secured and the lever operation is not inhibited. For example, Patent Literature 2: Jpn. Pat. Appln. KOKAI Publication No. 2004-321612 discloses an endoscope in which a joystick lever portion is covered with an elastic cover member (e.g. rubber cover or a rubber boot) which is fitted into a central hole in a watertight manner and the peripheral edge portion of the boot is pressed and fixed on an operating section exterior member by a substantially ring-shaped fixing member. With this structure, the operating section secures its water-tightness and the flexible rubber boot is deformed when the lever is tilted, with the result that the bending operation can be performed comfortably without inhibiting the lever operation.

Accordingly, it is an object of the present invention to provide an endoscope which prevents an elastic cover member of a joystick-type operating section from being twisted when the elastic cover member is fixed on the main body of the operating section and prevents the elastic cover member from being entangled when a joystick lever is operated. In addition, it is an object to provide a small-sized light bending operation mechanism having a watertight structure and an endoscope having the bending operation mechanism.

According to the present invention, it is an object to provide an endoscope which prevents an elastic cover member of a joystick-type operating section from being twisted when the elastic cover member is fixed on the main body of the operating section and prevents the elastic cover member from being caught when a joystick lever is operated. In addition, it is an object to provide a small-sized light bending operation mechanism having a watertight structure and an endoscope having the bending operation mechanism.

BRIEF SUMMARY OF THE INVENTION

According to an embodiment of the present invention, there is provided an endoscope having a bending operation mechanism, the endoscope including an operating section to give an instruction to bend a bending section provided on a distal end side of an elongated insertion section, the endoscope comprising: an operating lever having one end as a fulcrum and the other end, the other end of the operating lever being tiltable in all directions centering around the fulcrum; a frame section including the fulcrum and an opening in which the operating lever is placed and a frame wall portion is formed at a tip of the opening, the frame section including a locking section on an outer peripheral side thereof; a tilt regulation member placed in the frame section and having a first hole portion to regulate a tilt range of the operating lever; a boot section including a watertight fixing portion attached to an outer surface of the frame wall portion to cover the opening of the frame section in a watertight manner by causing the operating lever to pass through the opening; a first fixing member engaged with the locking section of the frame section and locked unrotatably in the watertight fixing portion of the boot section to press the watertight fixing portion from an outer periphery side such that the watertight fixing portion is made watertight; and a second fixing member screwed with the frame section to fix the first fixing member on the frame section.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 8 is a diagram showing a cross-sectional structure of a bending operation mechanism of a third embodiment.

DETAILED DESCRIPTION OF THE PREFERRED EMBODIMENT

Embodiments of the present invention will be described in detail below with reference to the drawings.

First Embodiment

Figure 1:
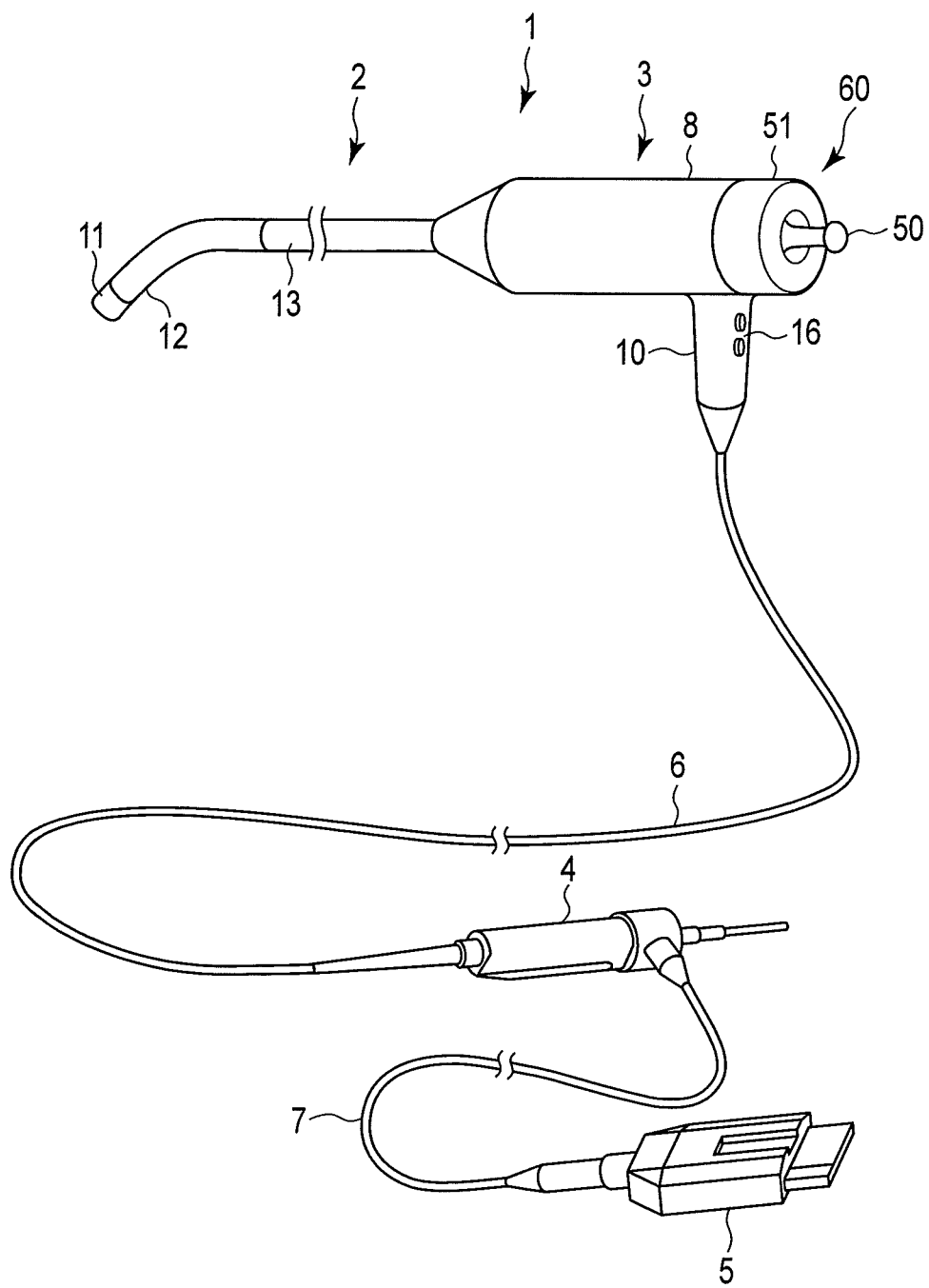
FIG. 1 is a diagram showing an example of a conceptual structure of an endoscope according to a first embodiment.

FIG. 1 shows an example of a conceptual structure of an endoscope 1 according to a first embodiment.

The endoscope 1 of the present embodiment chiefly includes an elongated flexible insertion section 2 to be inserted into a body cavity, an operating section 3 connected to the proximal end of the insertion section 2, a light guide connector 4 connected to a light source device (not shown), and a video connector 5 connected to a video system center (not shown). In the endoscope 1, the operating section 3 and the light guide connector 4 are connected through a flexible cable 6 as a universal cord, and the light guide connector 4 and the video connector 5 are connected through a communication cable 7.

The insertion section 2 includes a distal end portion 11 cylindrically formed chiefly of a metallic member such as stainless steel, a bending section 12, and a rigid tube 13 of a metal tube such as stainless steel, which are connected in sequence from the distal end of the insertion section. The end face of the rigid tube 13 to be inserted into a body cavity is provided with an irradiation window for illumination light and an image-pickup section, and the insertion section 2 includes a signal cable for video signals, a light guide and the like.

The operating section 3 includes a bending operation mechanism 60 that is a bending operation section to operate the bending section 12 remotely and various switches 16 to perform a variety of functions by the foregoing light source device and video system center. The bending operation mechanism 60 is provided at the proximal end portion of the operating section 3 (on the back side opposed to the insertion section 2). In the following descriptions, one side of the operating section 3 on which the insertion section 2 is provided will be referred to as a distal end side, and the other side thereof on which the bending operation mechanism 60 is provided will be referred to as a proximal end side. Moreover, a grip 10 from which the flexible cable 6 extends is provided to extend from the lateral side of the proximal end portion. The endoscope 1 is so configured that the bending section 12 is freely bent in four directions of up, down, right and left directions and the combination of these directions (referred to as all directions hereinafter) by the tilt operation of a joystick lever 50 of the bending operation mechanism 60.

The bending operation mechanism 60 of the present embodiment will be described below.

Figure 2:
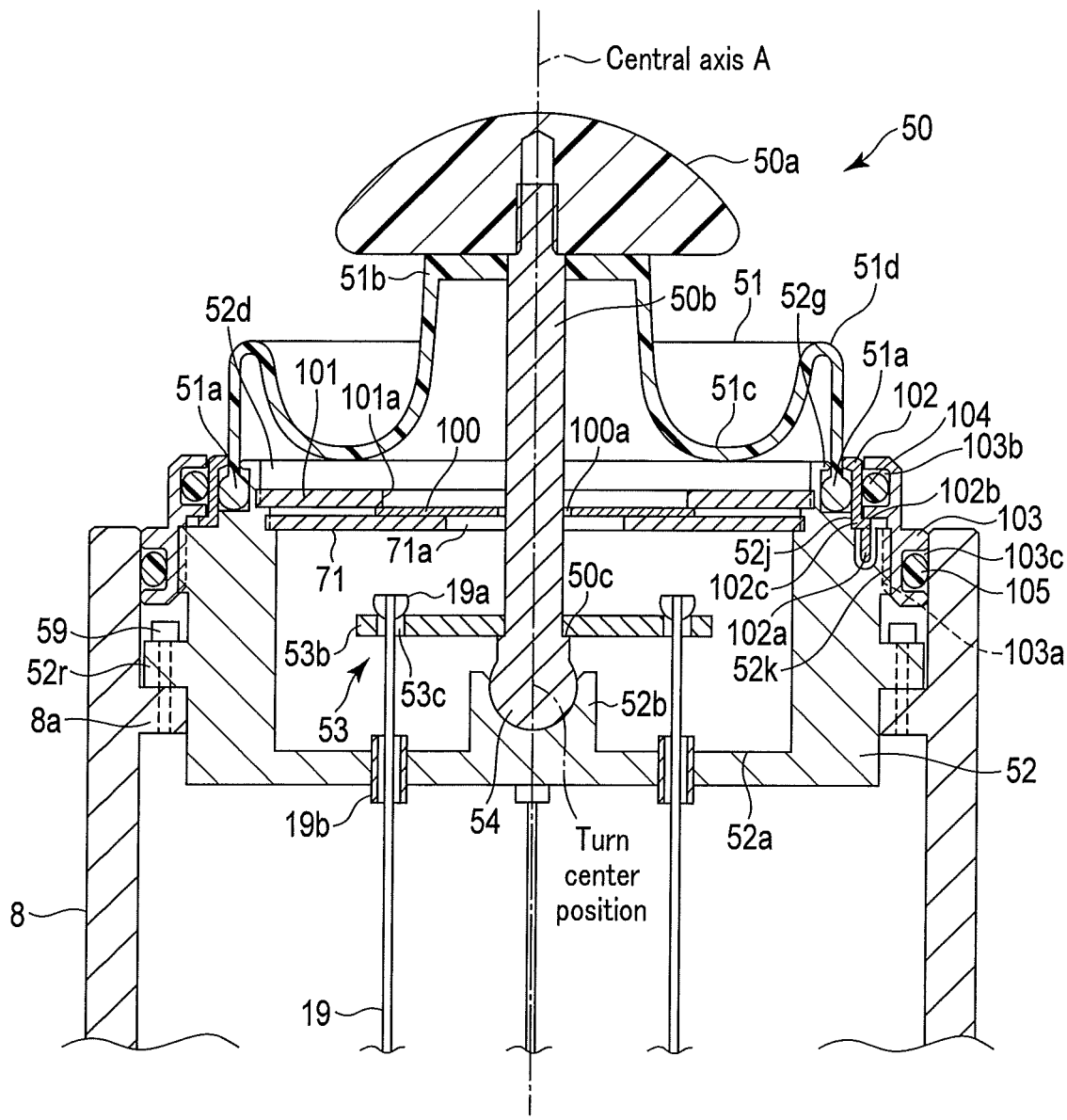
FIG. 2 is a diagram showing a cross-sectional structure of a bending operation mechanism of the first embodiment.
Figure 3:
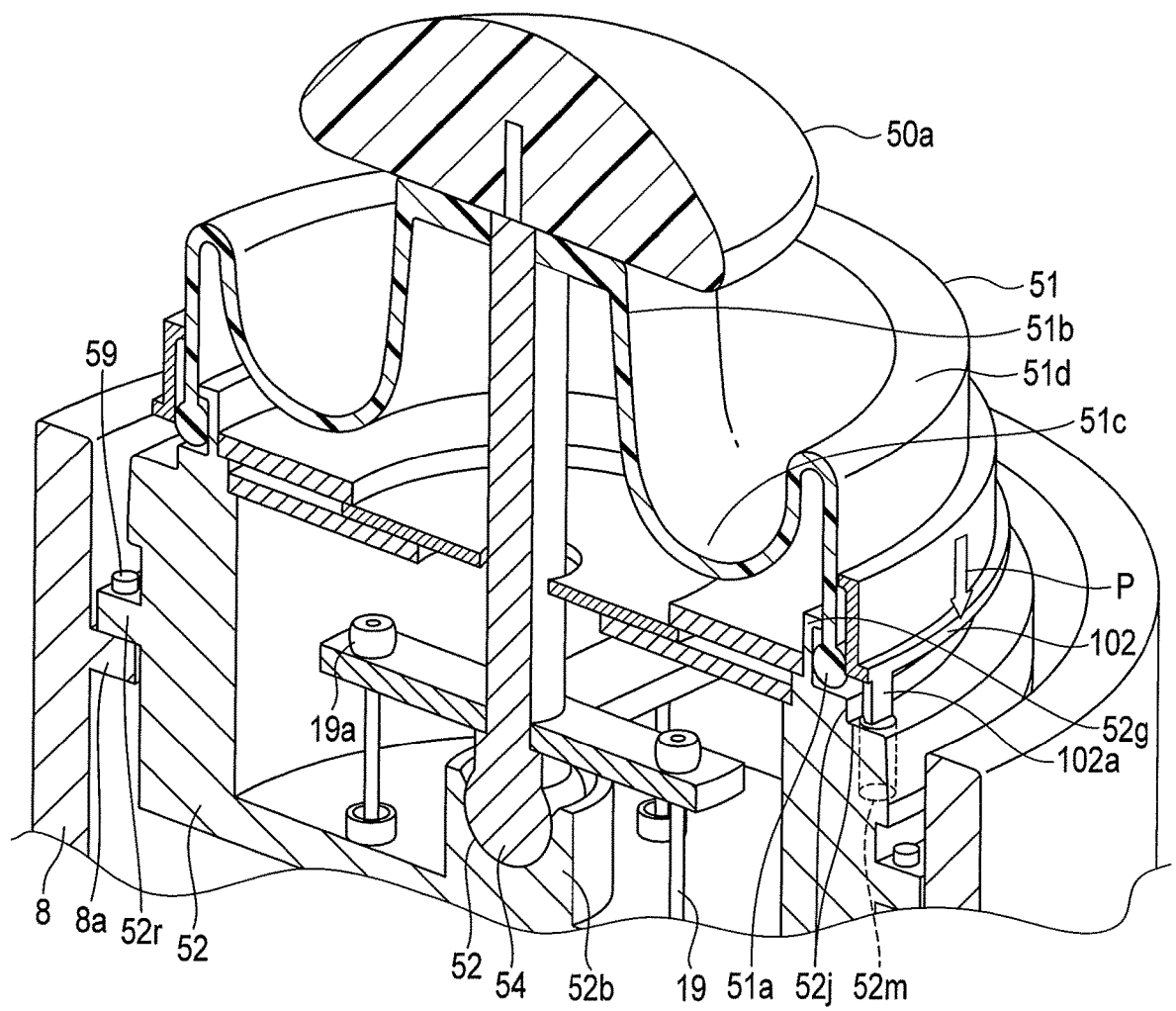
FIG. 3 is a perspective diagram showing a cross-sectional structure of the bending operation mechanism of the first embodiment when viewed from the oblique direction.
Figure 4:
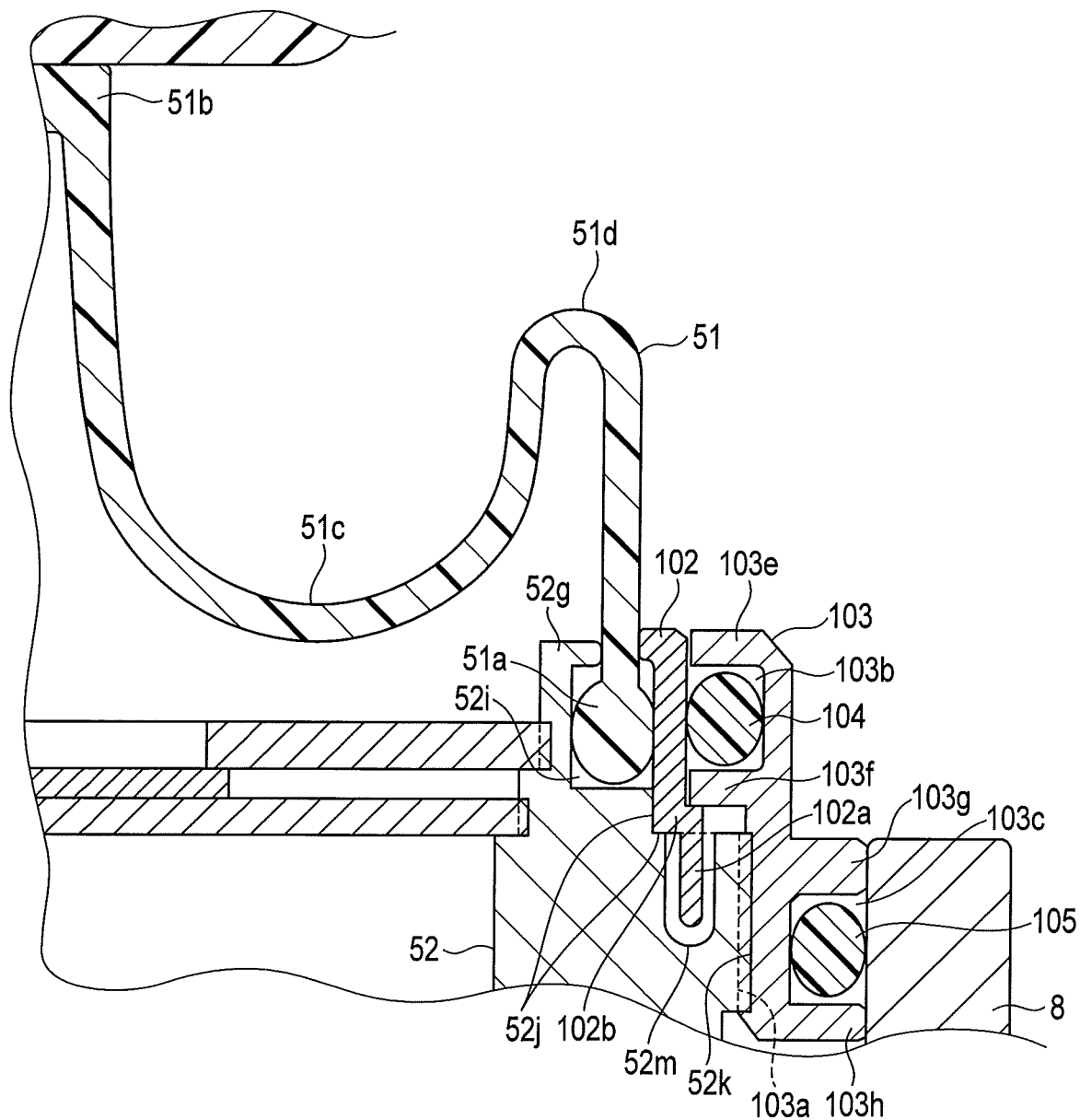
FIG. 4 is a diagram showing a cross-sectional structure of a portion to which a boot fixing ring and a pressing ring are added.

FIG. 2 is a diagram showing a cross-sectional structure of the bending operation mechanism, FIG. 3 is a perspective diagram showing a cross-sectional structure of the bending operation mechanism when viewed from the oblique direction, and FIG. 4 is a diagram showing a cross-sectional structure of a portion to which a boot fixing ring and a pressing ring are added.

The bending operation mechanism 60 of the present embodiment is placed on the proximal end side of a housing 8 [operating section exterior member] of the operating section 3. Needless to say, the position of the placement is not limited to the proximal end side, but it can be provided on the side surface of the housing 8 or a projecting portion formed to project from the side surface unless it impairs the operability.

The bending operation mechanism 60 includes the joystick lever 50 [operating lever], a rubber boot [boot section] 51 that is a cover member formed of an elastic material, a frame section 52 serving as a mechanism casing, and a wire pulling section 53 to bend the bending section. Of these sections, the frame section 52 is formed of a metallic material or a rigid resin material and shaped like a cylinder with a bottom (shaped like a cup), and an opening 52d is formed in the top of the frame section 52 and covered with the rubber boot 51.

A projecting portion 52r having a plurality of screw holes on its outer surface is formed on the entire outer surface of the frame section 52, and a projecting portion 8a overlapping the projecting portion 52r is formed on the entire inner surface of the housing 8. When the frame section 52 is fitted into the housing 8 such that the projecting portion 52r and the projecting portion 8a overlap each other, screw holes corresponding to the screw holes of the projecting portion 52r are formed in the projecting portion 8a, too, and these screw holes are screwed by screws 59 to fix the frame section 52 in the housing 8. Since, furthermore, the projecting portion 52r and the projecting portion 8a are bonded using the screws by interposing a seal member between them, the watertight structure can be achieved between the housing 8 and the frame section 52. In this case, the O-shaped ring used in a pressing ring 103, described later, is unnecessary.

The rubber boot 51 is shaped like a cap covering the circumference of the opening with the distal end portion of the joystick lever 50 exposed outwardly. The shape of the circumference of the rubber boot 51 matches that of the opening of the frame section 52. Here, the circumference of the rubber boot 51 is circular. The rubber boot 51 has such a section that the center of the boot is raised like a trapezoid to form a central part 51b having a flat surface, and the circumference of the boot rises substantially vertically from a peripheral edge portion 51a [watertight fixing portion] to have an annular, wavy, concave shape (roundish concave portion 51c) between the peripheral edge portion 51a and the central part 51b as shown in FIG. 4. Particularly, the waveform (the roundness of a semicircle) of a roundish convex portion 51d which leads to the roundish concave portion 51c from a portion of the edge side wall is formed small, and the roundness (the roundness of a semicircle) of the bottom of the roundish concave portion 51c is formed larger than the roundish convex portion 51d.

As described above, the rubber boot 51 prevents the joystick lever 50 from increasing in its operating force by increasing the waveform of the tilt range of the joystick lever 50 and decreasing the waveform of the outer periphery side, thereby improving the ability to hold a shape against a crush from the outer periphery side. If, furthermore, the roundness of the bottom of the roundish concave portion 51c is increased, an irrigation solution flows and circulates smoothly and, for example, dirt can be removed more easily.

In the center of the flat central part 51b, a hole through which the joystick lever 50 passes is formed. The hole and the joystick lever 50 are bonded in a watertight manner to prevent a liquid (e.g. blood and irrigation solution) from going into the frame section 52.

Furthermore, the peripheral edge portion 51a of the rubber boot 51 is thick and the section thereof is circular to have the function of an O-shaped ring to achieve a watertight structure. The peripheral edge portion 51a is placed in a groove 52i formed by a boot fixing ring 102, described later, and a frame wall portion 52g and crushed by pressure of both the walls, thus achieving a watertight structure in the frame section 52.

The joystick lever 50 includes a finger hook portion 50a for hooking an operator's finger, a rod 50b and a spherical portion 54. The rod 50b is substantially cylindrical and tapered from its proximal end portion placed in the frame section 52 toward its distal end portion exposed outwardly, and the proximal end side is provided with a step 50c to lock the wire pulling section 53. The finger hook portion 50a is semicircular and attached to the distal end portion of the rod 50b exposed outwardly. Furthermore, the spherical portion 54 is formed to lead to the step 50c at the proximal end of the rod 50b.

The spherical portion 54 is fitted turnably in a sphere receiving portion 52b provided substantially in the center of the bottom surface 52a of the frame section 52 to hold the rod 50b movably. In the present embodiment, as a movable mechanism of the joystick lever 50, a ball joint mechanism including the spherical portion 54 and the sphere receiving portion 52b is employed. In the following description, the central position of turn by the spherical portion 54 and sphere receiving portion 52b of the ball joint mechanism will be referred to as a fulcrum (or a fulcrum position). Moreover, the wire pulling section 53 is fitted from the distal end side of the rod 50b and bonded and fixed to the step 50c of the proximal end in an abutting state. The movable mechanism is not limited to the ball joint mechanism, but for example, a publicly known mechanism such as a mechanism pivotally supported by two shafts intersecting at right angles can be employed.

If, in the above structure, the joystick lever 50 is tilted, the wire pulling section 53 is shaken in arbitrary directions (all directions) centering around the fulcrum when the central axis A of the rod 50b is in a vertical direction (angle of 0°). A tilt regulation member 71 is placed in the opening 52d of the frame section 52 to set an inclination angle range (or an inclination range) of the joystick lever 50 based on the diameter of a hole 71a. FIG. 2 of the present embodiment shows a structure including an entanglement prevention mechanism of a third embodiment described later; however, in the first embodiment, the entanglement prevention mechanism can be provided or need not be done. If the entanglement prevention mechanism is provided, the third embodiment will bring about a greater advantage.

The wire pulling section 53 includes four pulling arm portions 53b shaped like a cross (see FIG. 3) such that the rod 50b is fitted into the intersection of the pulling portions, and a locking hole 53c is formed close to an end portion of each of the pulling arm portions 53b. On the bottom surface 52a of the frame section 52, a hole is formed in a position opposed to the locking hole 53c in parallel to the central axis A when the angle is 0°, and a coil pipe 19b is fitted and fixed into the hole.

A locking member 19a, which is provided at one end of a bending operation wire 19 guided through the coil pipe 19b, is locked into the locking hole 53c. When the locking member is locked, the bending operation wire 19 extending to the bending section 12 is pulled and loosened in accordance with a tilt of the pulling arm portions 53b. The bending section 12 is bent in all directions if a plurality of bending pieces (not shown) provided inside are turned in accordance with a state in which each of the bending operation wires 19 is pulled and loosened.

The frame wall portion 52g is formed to protrude from the top of the outer surface of the frame section 52, and a brim portion is formed at the distal end portion of the frame wall portion to extend toward the outer surface. The brim portion serves to prevent the peripheral edge portion 51a of the rubber boot 51 from being removed from the groove 52i formed by a boot fixing ring 102 and frame wall portion 52g, which will be described later.

As shown in FIG. 4, a fitting portion 52j having a side surface and a flat surface is provided to lower from a flat surface corresponding to the undersurface of the groove 52i of the frame wall portion 52g through a step. The boot fixing ring 102 is fitted to the fitting portion 52j. The fitting portion 52j has a diameter larger than that of the groove 52i, and at least one positioning hole 52m [concave portion] is formed in the flat surface of the fitting portion 52j. The positioning hole 52m is not limited to a cylindrical hole but may be a square hole or a notched groove 52n notched from the outer peripheral side, as described later with reference to FIG. 8.

Furthermore, a male screw 52k is formed on the side surface continuing downward from the flat surface of the fitting portion 52j through the step. The pressing ring 103, described later, is screwed to the male screw 52k.

The boot fixing ring 102 [first fixing member] is shaped like a cylinder having a crank-shaped section, and a brim is formed at the end of the boot fixing ring 102 to overhang the inner peripheral side to prevent the peripheral edge portion 51a from being removed from the groove 52i as described above. Furthermore, a flange portion 102b is formed to overhang the outer peripheral side at the lower end of the boot fixing ring 102. The flange portion 102b includes a hook 102a [convex portion] fitted into the corresponding positioning hole 52m.

As shown in FIG. 3, after the peripheral edge portion 51a of the rubber boot 51 is attached to the frame wall portion 52g, the boot fixing ring 102 is externally fitted to the fitting portion 52j from above such that the hook 102a is fitted into the hole 52m. If the hook 102a is fitted into the hole 52m and positioned, the fitting state is held to prevent the boot fixing ring 102 from turning when the pressing ring 103 described later is screwed. If the boot fixing ring 102 is so fitted, the peripheral edge portion 51a of the rubber boot 51 fitted between the inner surface of the boot fixing ring 102 and the undersurface of the groove 52i or the outer surface of the frame wall portion 52g is crushed. The peripheral edge portion 51a serves as an O-shaped ring in a watertight state and prevents a liquid from going into the frame section 52 from outside.

Furthermore, as shown in FIG. 4, the pressing ring 103 [second fixing member] is screwed to the male screw 52K to retain a watertight state by the boot fixing ring 102. The pressing ring 103 is shaped like a cylinder, overhangs the upper side of the inner surface, and includes two brim portions 103e and 103f used as groove walls to press the boot fixing ring 102. The brim portions 103e and 103f are separated from each other, and an interval between them is used as a groove 103b in which an O-shaped ring 104 is fitted. This O-shaped ring 104 prevents moisture, which enters from the screwed portion of the pressing ring 103 and the frame section 52 through a gap between the boot fixing ring 102 and the pressing ring 103 from outside, from going into the housing 8. With this screwing, the O-shaped ring 104 presses the upper part of the boot fixing ring 102 elastically in the radial direction, and the brim portion 103f supports the O-shaped ring 104 and presses and fixes the flange portion 102b on the fitting portion 52j located below.

Furthermore, the pressing ring 103 presses the boot fixing ring 102 from its outer surface side, and the O-shaped ring 104 causes a watertight state between the pressing ring 103 and the boot fixing ring 102. The pressing ring 103 overhangs the lower side of the outer surface and includes brim portions 103g and 103h to be supported against the frame section 52, and an interval between them is used as a groove 103c in which an O-shaped ring 105 is fitted. A female screw 103a screwed to the male screw 52k is formed in the inner surface corresponding to the underside of the brim portions 103g and 103h. The O-shaped ring 105 presses the housing 8 to retain a watertight state between the housing 8 and the pressing ring 103 and prevents a liquid from going into the housing 8 from outside.

As described above, the bending operation mechanism of the present embodiment has a watertight structure including the boot fixing ring 102 for achieving watertightness, which does not turn, and the pressing ring 103 to fix the boot fixing ring 102 on the frame section 52. In this watertight structure, when the pressing ring 103 is screwed and fixed to the frame section 52, it turns to exert its force on the boot fixing ring 102 via the O-shaped ring 104 in the turn direction. Then, the hook 102a of the boot fixing ring 102 is engaged with the hole 52m of the frame section 52 and thus the boot fixing ring 102 is prevented from turning. Thus, even though the pressing ring 103 is screwed, no rotation force is applied to the peripheral edge portion 51a.

Therefore, since the bending operation mechanism of the present embodiment has a watertight structure to prevent a liquid from going into the operation section, and prevents a twist from being caused between the peripheral edge portion 51a and central part 51b of the rubber boot 51, a nonuniform force is not applied to the joystick lever 50 due to a deformation of the rubber boot 51, with the result that a smooth lever tilt operation can be performed with an equal degree of force.

Modification to First Embodiment

Figure 5:
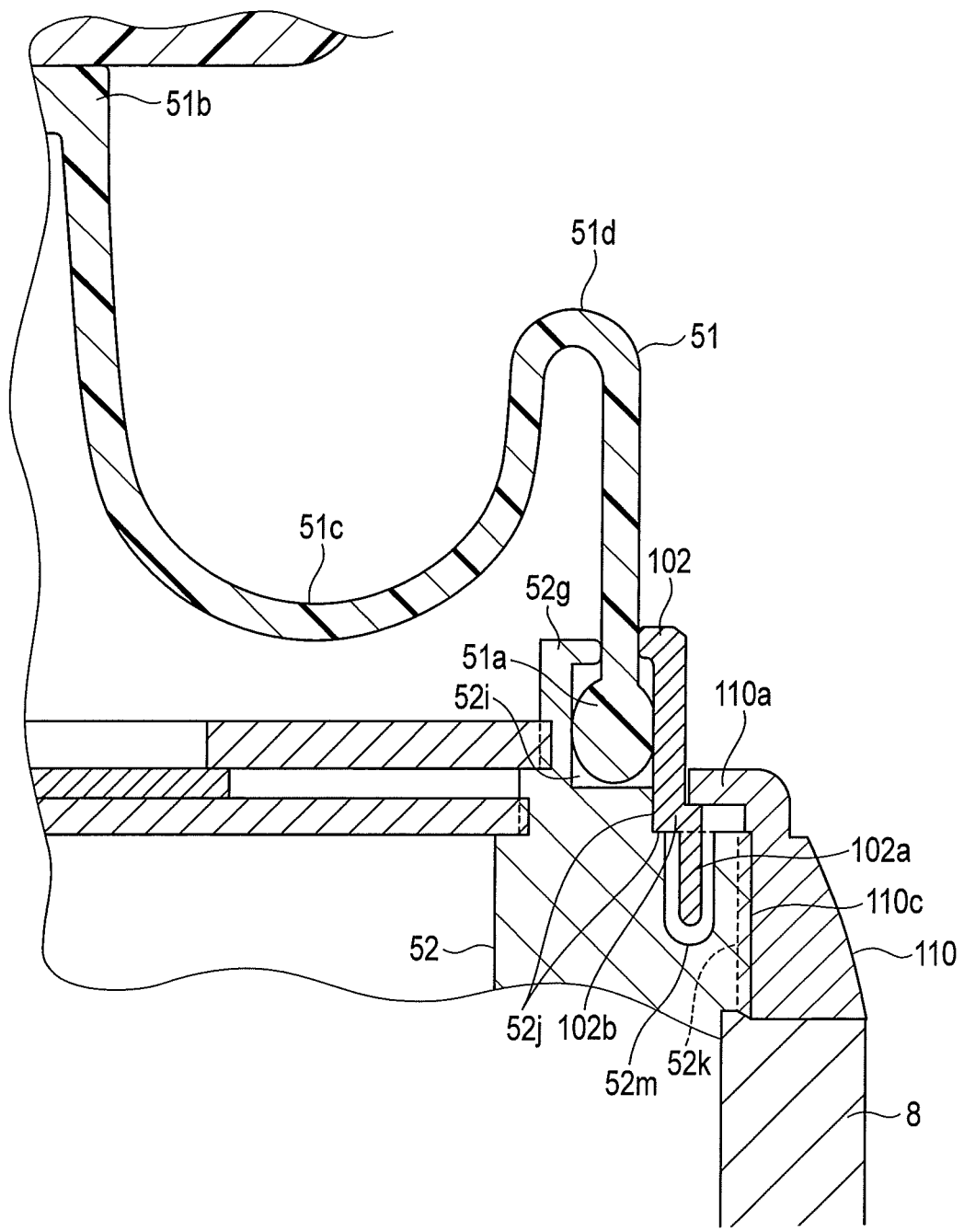
FIG. 5 is a diagram showing a cross-sectional structure of a bending operation mechanism of a modification to the first embodiment.

FIG. 5 shows a structure in which the housing 8 and the frame section 52 are directly bonded and fixed as a modification to the first embodiment. The foregoing first embodiment has a structure in which the housing 8 and the frame section 52 are rendered watertight by the O-shaped ring 105, whereas the modification has a structure in which the housing 8 and the frame section 52 are directly bonded and rendered watertight. In the present modification, the same structural elements as those of the foregoing first embodiment are denoted by the same reference sign and their detailed descriptions are omitted.

The present modification includes a pressing ring 110 excluding the O-shaped ring 104 of the pressing ring 103. As shown in FIG. 5, the pressing ring 110 includes a fixing portion 110a to fix the flange portion 102b under the outer periphery portion of the boot fixing ring 102 when the pressing ring 110 is screwed to the frame section 52. A fixing portion 110b prevents the flange portion 102b from rising and thus prevents the hook 102a formed on the undersurface of the flange portion 102b from being detached from the positioning hole 52m.

A female screw 110c screwed to the male screw 52k formed on the outer surface of the frame section 52 is formed on the inner surface side of the pressing ring 110.

In this modification, too, the advantage that is equivalent to that of the foregoing first embodiment can be obtained. Since, furthermore, neither of the O-shaped rings 104 and 105 used for the pressing ring 103 is required, the structure is simplified and the number of parts can be reduced.

Second Embodiment

Figure 6:
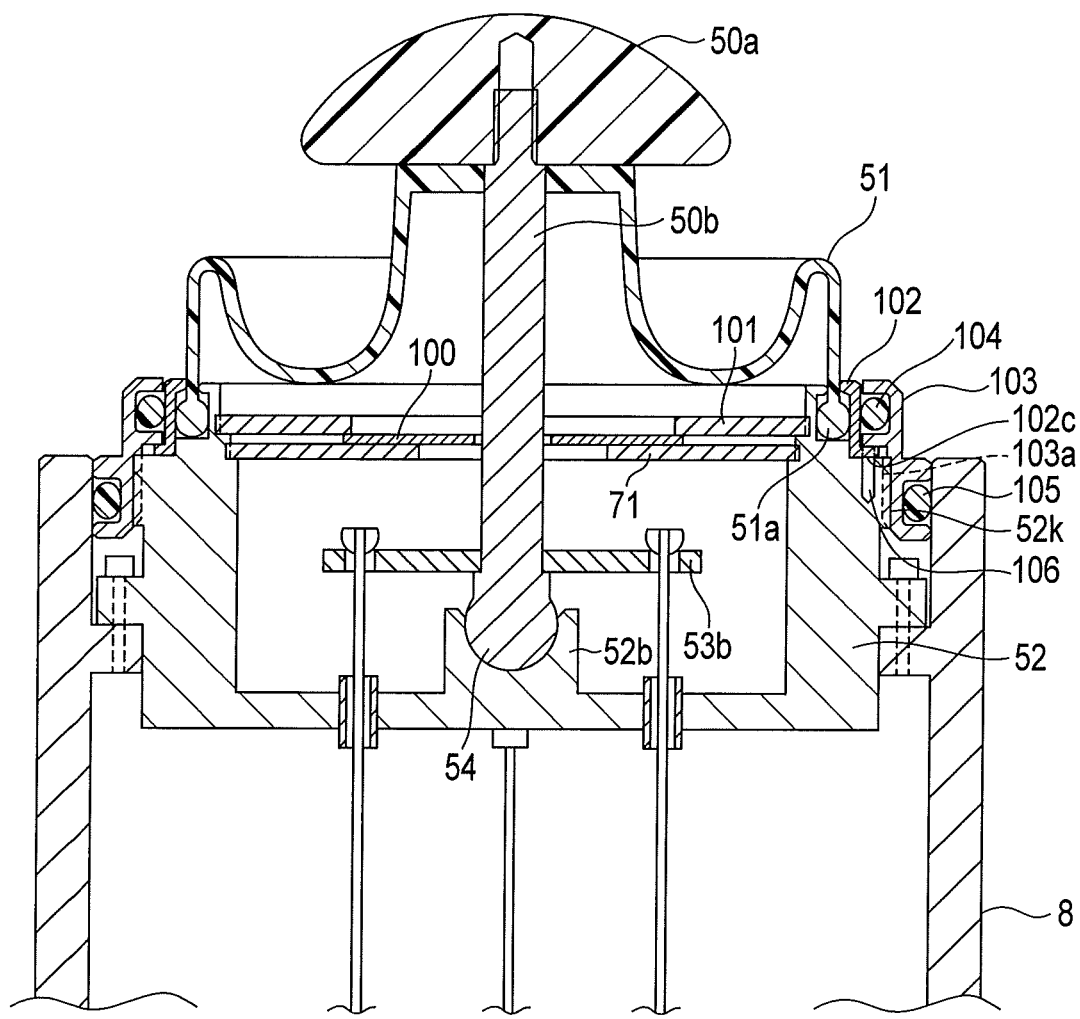
FIG. 6 is a diagram showing a cross-sectional structure of a bending operation mechanism of a second embodiment.
Figure 7:
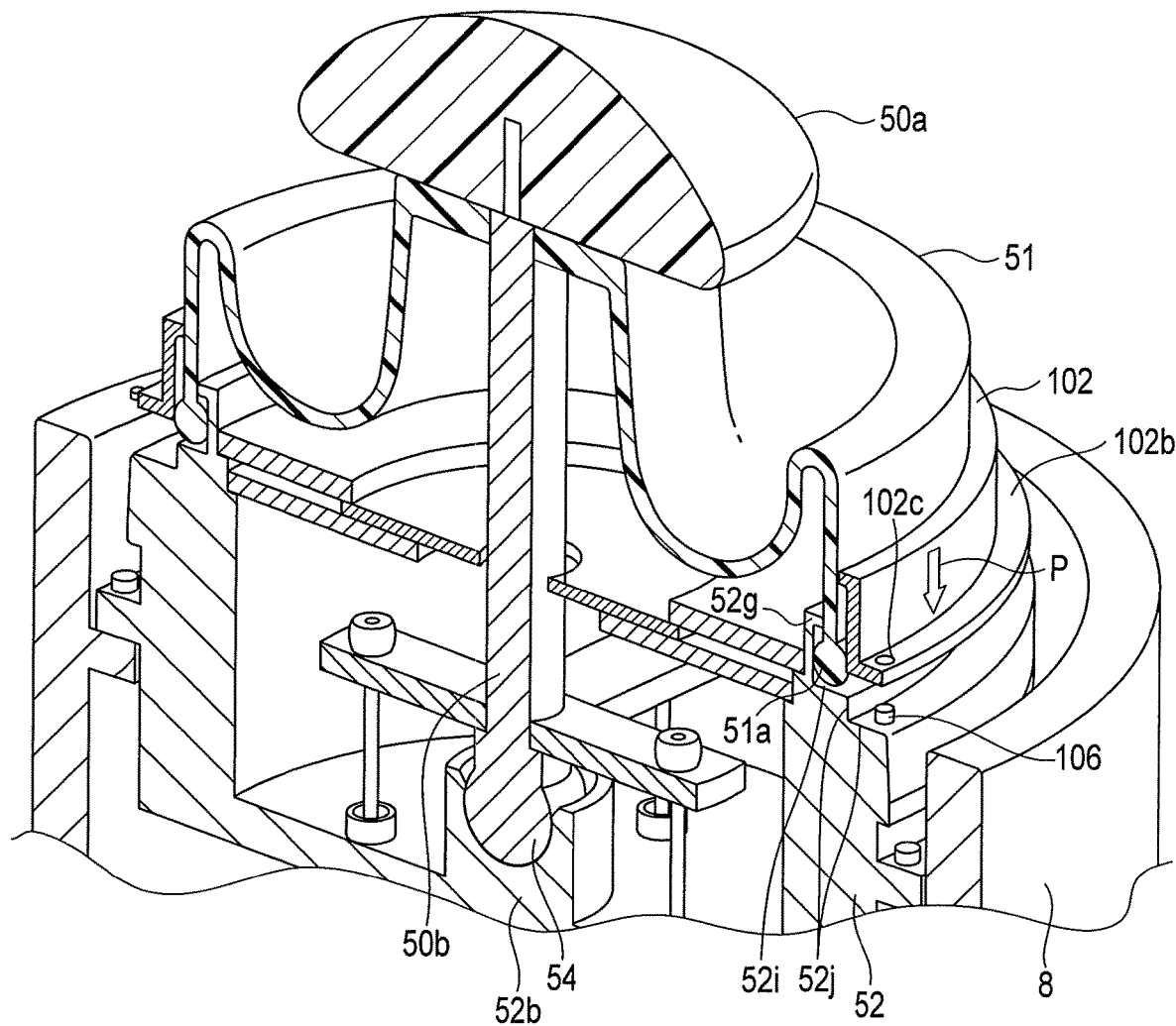
FIG. 7 is a perspective diagram showing a cross-sectional structure of the bending operation mechanism of the second embodiment when viewed from the oblique direction.

A second embodiment will be described below. FIG. 6 is a cross-sectional diagram of a bending operation mechanism 60 of the second embodiment. FIG. 7 is a perspective diagram of a section of a partly-enlarged component of the bending operation mechanism 60 of the second embodiment. The same structural elements as those of the foregoing first embodiment are denoted by the same reference sign and their detailed descriptions are omitted.

The present embodiment differs from the first embodiment in the structure to prevent the boot fixing ring 102 from rotating with respect to the frame sections 52. As shown in FIG. 6, at least one positioning pin 106 is fitted on the flat surface of the fitting portion 52j. A hole 102c fitted to the positioning pin 106 is formed in the flange portion 102b under the outer periphery portion of the boot fixing ring 102.

As shown in FIG. 7, after the peripheral edge portion 51a of the rubber boot 51 is fitted into the groove 52i, the positioning pin 106 is fitted into the hole 102c and the boot fixing ring 102 is externally fitted to the fitting portion 52j from above. When the pressing ring 103 is screwed and fixed to the frame section 52, it turns to exert its force on the boot fixing ring 102 via the O-shaped ring 104 in the turn direction. Then, the hole 102c of the boot fixing ring 102 is fitted to the positioning pin 106 of the frame section 52 and thus the boot fixing ring 102 is prevented from turning.

In the above-described watertight structure of the present embodiment, the boot fixing ring 102 to achieve watertightness for the peripheral edge portion 51a of the rubber boot 51 is prevented from rotating and its fixing state is held by fitting the positioning pin 106 into the hole 102c when the pressing ring 103 is screwed.

Thus, when the pressing ring 103 is screwed, no rotation force is applied to the peripheral edge portion 51a. Therefore, no twist is caused between the peripheral edge portion 51a and central part 51b of the rubber boot 51 or no nonuniform force is not applied to the joystick lever 50 due to a deformation of the rubber boot 51, with the result that a smooth lever tilt operation can be performed with the same degree of force.

Third Embodiment

A third embodiment will be described below. FIG. 8 is a cross-sectional view of a bending operation mechanism 60 of the third embodiment including an entanglement prevention mechanism. The same structural elements as those of the foregoing first embodiment are denoted by the same reference sign and their detailed descriptions are omitted. Since FIG. 2 also shows a structure including an entanglement prevention mechanism, the third embodiment will be described with reference to FIGS. 2 and 8.

The opening 52d of the frame section 52 includes a hole through which the rod 50b passes, and a tilt regulation member 71, a partition plate 100 and a pressing plate 101 are stacked one on another with a gap therebetween. A male screw is formed on the periphery of each of the tilt regulation member 71 and pressing plate 101 and screwed into the opening 52d. The partition plate 100 is so configured to move in the gap between the tilt regulation member 71 and pressing plate 101 in accordance with the tilt operation of the rod 50b.

As shown in FIG. 8, two steps of an upper step 52p and a lower step 52q are formed on the inner surface from the opening 52d toward the bottom. A female screw 52e is formed on the inner surface side of the frame wall portion 52g, and the upper step 52p is formed below the female screw. The surface of the upper step 52p corresponds to the placement surface of the pressing plate 101. Moreover, a female screw 52f is formed on the inner surface of the lower step 52q from the upper step 52p, and the surface of the lower step 52q corresponds to the placement surface of the tilt regulation member 71.

The tilt regulation member 71 is screwed to the female screw 52f and fixed on the surface of the lower step 52q. It is desirable to bond them partly with an adhesive or the like in order to prevent the screw from loosening thereafter. In the tilt regulation member 71, a hole 71a is opened to set a tilt angle (tilt range) of the joystick lever 50.

The partition plate 100 is placed on the tilt regulation member 71. In the partition plate 100, a hole 100a whose diameter is slightly larger than that of the rod 50b is opened. The diameter of the hole 100a is set such that a gap is formed between the hole 100a and the rod 50b to prevent the hole 100a from contacting the rod 50b passing through the hole 100a to perform a tilt operation. Furthermore, when the joystick lever 50 is tilted to the limit of tilt, the partition plate 100 does not abut on the inner surface of the frame section 52 but has a size not to expose the hole 71a. Furthermore, the partition plate 100 may have irregularities of very small dots and patterns on its front and rear surfaces to decrease the area of contact between the tilt regulation member 71 and the pressing plate 101, lower the frictional resistance, and reduce a load applied to the tilt operation.

The pressing plate 101 is screwed to the female screw 52e and fixed on the surface of the upper step 52p. It is desirable to bond them partly with an adhesive or the like in order to prevent the screw from loosening thereafter. In this fixing, the pressing plate 101 does not contact the partition plate 100 with a gap therebetween or they contact each other to such a degree that only a slight load is applied. The pressing plate 101 has a hole 101a having such a diameter that the rod 50b does not abut on the hole 71a even though the joystick lever 50 is tilted to the limit of tilt. These holes 71a, 100a and 101a are arranged such that their centers coincide with one another or they are arranged concentrically when the tilt angle of the joystick lever 50 is 0° (central axis A). The foregoing rubber boot 51 is attached to cover the opening 52d of the frame section 52.

In the present embodiment, the tilt regulation member 71 is fixed on the inner side of the opening 52d of the frame section 52 and the pressing plate 101 is placed on the outer side with the partition plate 100 therebetween.

As described in the foregoing item of "the objects of the invention," since the operating section is sterilized together with the insertion section after the endoscope is used, pressure is applied to the operating section by an irrigation solution or the like in the sterilization process and focused on the roundish concave portion 51c of the rubber boot 51 in terms of its shape if the endoscope has a bending operation mechanism. Thus, the edge sidewall falls inwardly, and the roundish concave portion 51c extends and approaches or contacts the frame section 52. As an entanglement prevention mechanism, the partition plate 100 to prevent the rubber boot 51 from going inside is provided on the top surface of the tilt regulation member 71.

According to the entanglement prevention mechanism of the present embodiment, when an external pressure is applied to the being mechanism or a negative pressure is caused in the operating section, even though the boot section made of an elastic member is extended by the pressure, the rubber boot 51 is not drawn into the frame section 52. Thus, the rubber boot is not entangled in the movable space of the operating section or it is not damaged. In the drawings of the foregoing first and second embodiments, a structure including the entanglement prevention mechanism is shown, but the entanglement prevention mechanism can be used alone or in combination.

What is claimed is:

1. An endoscope comprising:
an operating section housing a bending operation mechanism to give an instruction to bend a bending section provided on a distal end side of an elongated insertion section, the bending operation mechanism comprising:
an operating lever for providing the instruction to the bending section, the lever being tiltable with respect to a fulcrum;
a frame including the fulcrum, the frame having an opening through which the operating lever is placed, the frame having a frame wall formed at the opening, the frame including one of a positioning projection or hole on an outer peripheral side of the frame;
a boot disposed to cover the opening in the frame, the boot including a watertight fixing portion that contacts with an outer peripheral surface of the frame wall, the watertight fixing portion being provided in a peripheral portion of the boot and having a circular cross section;
a first fixing ring having an other of the positioning projection or hole engaged with the one of the positioning projection or hole of the frame, the first fixing ring having an interior surface pressing the watertight fixing portion in a radial direction of the opening, from an outer peripheral side of the watertight fixing portion of the boot toward the outer peripheral surface of the frame wall so as to maintain an inside of the frame watertight; and
a second fixing ring having a first threaded surface engaging a second threaded surface disposed on the outer peripheral surface of the frame, the second fixing ring sliding over an outer peripheral surface of the first fixing ring to engage the first threaded surface with the second threaded surface and to fix the first fixing ring by pressing the interior surface of the first fixing ring against the watertight fixing portion.

2. The endoscope according to claim 1, wherein
the second fixing ring is provided with a first groove facing the outer peripheral surface of the first fixing ring and a second groove facing a housing of the operating section;
a first sealing material is disposed between an interior surface of the first groove and the outer peripheral surface of the first fixing ring, and
a second sealing material is disposed between an interior surface of the second groove and the housing of the operating section.

3. The endoscope according to claim 1, wherein the bending operation mechanism further comprises:
a tilt regulation member placed in the frame and having a first hole to regulate a tilt range of the operating lever;
a partition movably placed on the tilt regulation member; and a pressing member placed on the partition, the pressing member being fixed in the opening and the pressing member having a second hole whose diameter is larger than that of the first hole.

\* \* \* \* \*